(12) United States Patent
Zhang et al.

(10) Patent No.: US 11,925,557 B1
(45) Date of Patent: Mar. 12, 2024

(54) SHEATH FACILITATING RETRACTION OF PROSTHETIC IMPLANT AND DELIVERY SYSTEM

(71) Applicant: VENUS MEDTECH (HANGZHOU) INC., Zhejiang (CN)

(72) Inventors: Zhifei Zhang, Zhejiang (CN); Jianan Wang, Zhejiang (CN); Meirong Liu, Zhejiang (CN)

(73) Assignee: VENUS MEDTECH (HANGZHOU) INC., Hangzhou (CN)

( * ) Notice: Subject to any disclaimer, the term of this patent is extended or adjusted under 35 U.S.C. 154(b) by 0 days.

(21) Appl. No.: 18/215,840

(22) Filed: Jun. 29, 2023

Related U.S. Application Data (63) Continuation of application No. PCT/CN2023/101132, filed on Jun. 19, 2023.

(30) Foreign Application Priority Data

Apr. 11, 2023 (CN) .......................... 202310375811.9

(51) Int. Cl.
*A61F 2/24* (2006.01)

(52) U.S. Cl.
CPC .................. *A61F 2/2436* (2013.01)

(58) Field of Classification Search
CPC ...... A61F 2002/9528; A61F 2002/9534; A61F 2230/0067; A61F 2/2436; A61F 2/9522; A61M 25/0074
See application file for complete search history.

(56) References Cited

U.S. PATENT DOCUMENTS

| | | | | |
|---|---|---|---|---|
| 2011/0098804 | A1* | 4/2011 | Yeung | A61F 2/2412 623/2.1 |
| 2022/0000645 | A1* | 1/2022 | Song | A61F 2/962 |
| 2022/0395667 | A1* | 12/2022 | Keating | A61M 25/0074 |
| 2023/0038490 | A1 | 2/2023 | Griswold et al. | |

FOREIGN PATENT DOCUMENTS

KR 20200025130 A 3/2020

OTHER PUBLICATIONS

Office Action dated May 24, 2023 for corresponding Chinese Application No. 202310375811.9 along its English Translation, 7 pages.

* cited by examiner

*Primary Examiner* — Kelly J Bekker
*Assistant Examiner* — Andrew P. Restaino

(57) ABSTRACT

A sheath facilitating retraction of prosthetic implant is provided. The sheath includes a tubular body, and the distal end of the body is connected with an expandable section. The expandable section has relative converged configuration and flared configuration and includes a primary expandable area and a secondary expandable area. The primary expandable area includes a plurality of first expandable pieces arranged at intervals in a circumferential direction of the body. The secondary expandable area includes a plurality of second expandable pieces arranged at intervals in the circumferential direction of the body, and all the second expandable pieces include two alternating groups consisting of a first group formed by further extending the first expandable pieces to the distal end and a second group formed by connecting strips wound between two adjacent first expandable pieces.

14 Claims, 7 Drawing Sheets

SHEATH FACILITATING RETRACTION OF PROSTHETIC IMPLANT AND DELIVERY SYSTEM

CROSS-REFERENCE TO RELATED APPLICATIONS

The present application is a Continuation Application of PCT Application No. PCT/CN2023/101132, filed on Jun. 19, 2023, which claims the priority of Chinese Application No. 202310375811.9, filed on Apr. 11, 2023, the entire contents of which are hereby incorporated by reference.

TECHNICAL FIELD

The present disclosure relates to the technical field of medical device, in particular to a sheath facilitating retraction of prosthetic implant and a delivery system.

DESCRIPTION OF THE PRIOR ART

A diseased or defected heart valve can be repaired or replaced by implanting a prosthetic heart valve (hereinafter, prosthetic implant). The prosthetic implant is loaded at the distal end of the delivery system, and is delivered to the surgical site by intervention of the delivery system. If the prosthetic implant is improperly positioned within the native valve annulus during the expansion process, serious complications may occur.

The existing method is to recapture the prosthetic implant, that is, to recompress and reposition the completely or partially expanded prosthetic implant into the sheath of the delivery system. This process can also be called the retraction of the prosthetic implant. The term "retraction" and "recapture" here refer to the same meaning. After being retracted, the prosthetic implant is withdrawn outside the human body or repositioned in the human body.

Although the existing configuration of the sheath can retract the prosthetic implant, the retracting operation is still stuck and unsmooth. Therefore, it is necessary to optimize the configuration of the sheath.

SUMMARY OF THE INVENTION

The present disclosure provides a sheath facilitating retraction of prosthetic implant, to improve the smoothness of the retraction operation.

The present disclosure provides a sheath facilitating retraction of prosthetic implant, including a tubular body which has opposing distal and proximal ends along its own axial direction. The distal end of the body is connected with an expandable section which has relative converged configuration and flared configuration and includes from the proximal end to the distal end in sequence:
  a primary expandable area, including a plurality of first expandable pieces arranged at intervals in a circumferential direction of the body; and
  a secondary expandable area, including a plurality of second expandable pieces arranged at intervals in the circumferential direction of the body, wherein all the second expandable pieces include two alternating groups consisting of a first group formed by further extending the first expandable pieces to the distal end and a second group formed by connecting strips wound between two adjacent first expandable pieces.

In the following, several alternatives are provided, but merely as further additions or preferences, instead of as additional limitations to the above-mentioned technical solution. Without technical or logical contradiction, the alternatives can be combined with the above-mentioned technical solution, individually or in combination.

Optionally, in the flared configuration of the expandable section, the primary expandable area and the secondary expandable area have respective flare angles relative to the axial direction of the body, and the flare angle of the secondary expandable area is greater than the flare angle of the primary expandable area.

Optionally, all the second expandable pieces have the same outer contour and are uniformly spaced in the circumferential direction.

Optionally, the outer contour of the second expandable piece gradually widens from the proximal end to the distal end.

Optionally, the first expandable piece gradually narrows from the proximal end toward the distal end until being connected with the corresponding second expandable piece in the second group.

Optionally, in the axial direction of the body, the first expandable piece has a length being 60-80% of a length of the expandable section.

Optionally, an end of the connecting strip is connected to a junction of the first expandable piece and the corresponding second expandable piece.

Optionally, the connecting strip is wound in an $\Omega$ shape, and an opening of the shape faces towards the proximal end.

Optionally, two adjacent first expandable pieces and the second expandable pieces between the two adjacent first expandable pieces enclose a first hollow area, in the axial direction of the body, the first hollow area has a length being greater than 90% of a length of the expandable section.

Optionally, within the secondary expandable area, the second expandable piece in the first group has a second hollow area adjacent to the distal end thereof, and the second expandable piece in the second group has a third hollow area.

Optionally, the third hollow area has an area (i.e., the amount of space covered by the third hollow area) larger than an area (i.e., the amount of space covered by the second hollow area) of the second hollow area.

Optionally, within the primary expandable area, a fourth hollow area is defined between two adjacent first expandable pieces, and the fourth hollow area has an area (i.e., the amount of space covered by the fourth hollow area) larger than the area of the third hollow area.

Optionally, the body further comprises a metal reinforcement layer formed in one piece with the expandable section, and the metal reinforcement layer is connected with the proximal end of the expandable section. Optionally, the metal reinforcement layer is a non-expandable section.

Optionally, the metal reinforcement layer and all expandable pieces are formed in one piece by cutting a tube.

Optionally, inner and outer sides of the metal reinforcement layer are provided with polymer covering film layers, and the polymer covering film layers extend to the distal end to cover inner and outer sides of the expandable section.

The disclosure further provides a delivery system, including:
  a catheter assembly, which includes the above-mentioned sheath facilitating retraction of prosthetic implant and an inner shaft assembly, the prosthetic implant being connected to a distal end of the inner shaft assembly; and
  a control handle, a proximal end of the catheter assembly is connected to and controlled by the control handle.

The connecting strips of the sheath of the present disclosure allow the secondary expandable area and the primary expandable area to have different flare ranges, so that the secondary expandable area and the primary expandable area can conform to the compressed profile of the prosthetic implant at various positions and thus improve the smoothness of retraction.

LIST OF REFERENCE SIGNS

1000, sheath; 101, proximal end; 102, distal end;
110, body; 111, polymer covering film layer; 112, metal reinforcement layer; 113, fifth hollow area;
120, expandable section; 130, primary expandable area; 131, first expandable piece;
140, secondary expandable area; 141, elastic tab; 142, connecting strip; 143, opening; 151, first hollow area; 152, second hollow area; 153, third hollow area; 154, fourth hollow area;
181, first position; 182, second position; 190, dash-dotted line;
2000, delivery system; 210, catheter assembly; 220, control handle; 230, inner shaft assembly;
3, prosthetic implant.

DESCRIPTION OF EMBODIMENTS

The technical solutions according to the embodiments of the present disclosure will be described clearly and fully in combination with the drawings according to the embodiments of the present disclosure. Obviously, the described embodiments are not all embodiments of the present disclosure, but only part of the embodiments of the present disclosure. Based on the disclosed embodiments, all other embodiments obtained by those skilled in the art without creative work fall into the scope of this invention.

It should be noted that, when a component is "connected" with another component, it may be directly connected to another component or may be indirectly connected to another component through a further component. When a component is "provided" on another component, it may be directly provided on another component or may be provided on another component through a further component.

Unless otherwise defined, all technical and scientific terms used herein have the same meaning as commonly understood by a person skilled in the art. The terms in the description of the present disclosure are used to describe specific embodiments, and not to limit the present disclosure. The term "and/or" used herein includes one or more of the listed options in any combinations, or the combination of all of the listed options.

In the present disclosure, the terms "first", "second" and the like are used for descriptive purposes only and are not to be understood as indicating or implying the relative importance or the number or order of the technical features referred. Thus, features defined with "first", "second" can explicitly or implicitly include one or more of such features. In the description of the present invention, "plurality" means at least two, such as two, three, etc., unless explicitly and specifically defined otherwise.

In the following drawings or descriptions, the prosthetic implant uses a prosthetic heart valve as an example. The prosthetic heart valve generally includes a deformable stent and leaflets connected within the stent. The stent is generally cylindrical, and the side wall thereof has a hollow meshed structure. Unless otherwise specified, the shape or size of the meshed structure is not strictly limited. The interior of the stent is a blood flow channel, and the leaflets cooperate with each other to open and control the blood flow channel within the stent. For positioning in the human body, the stent can be provided with positioning structures at the periphery, such as anchors, arms, and the like, that can engage with the surrounding native tissue.

The stent can be controlled by a wire, so that it can be retracted as desired during the release process. The stent can be formed by cutting a tube or braiding wires, and the leaflets can be connected to the stent by sewing, bonding or molding.

The stent generally has a connecting structure for engaging with the catheter assembly to limit each other, thereby preventing undesired deflection during delivery. The prosthetic implant has a radially compressed configuration during the interventional delivery, i.e., a loaded state, and a released state after being released from the catheter assembly and radially expanded in the human body.

For direction reference, the proximal end herein generally refers to the side adjacent to the operator (such as the physician), and the distal end refers to the side that is relatively far away from the operator. Each component has its own opposing distal and proximal ends in the intervention path. In theory, when the catheter assembly and the control handle are completely straightened, the straight line between the proximal end and the distal end defines the axis and thus the axial direction, and then the radial direction perpendicular to the axial direction and the circumferential direction around the axial direction can be determined. For structure reference, "end" herein refers to an end face of the structure or a certain point or a certain area at the corresponding side or a specific structure connected to the point or the area.

Figure 1:
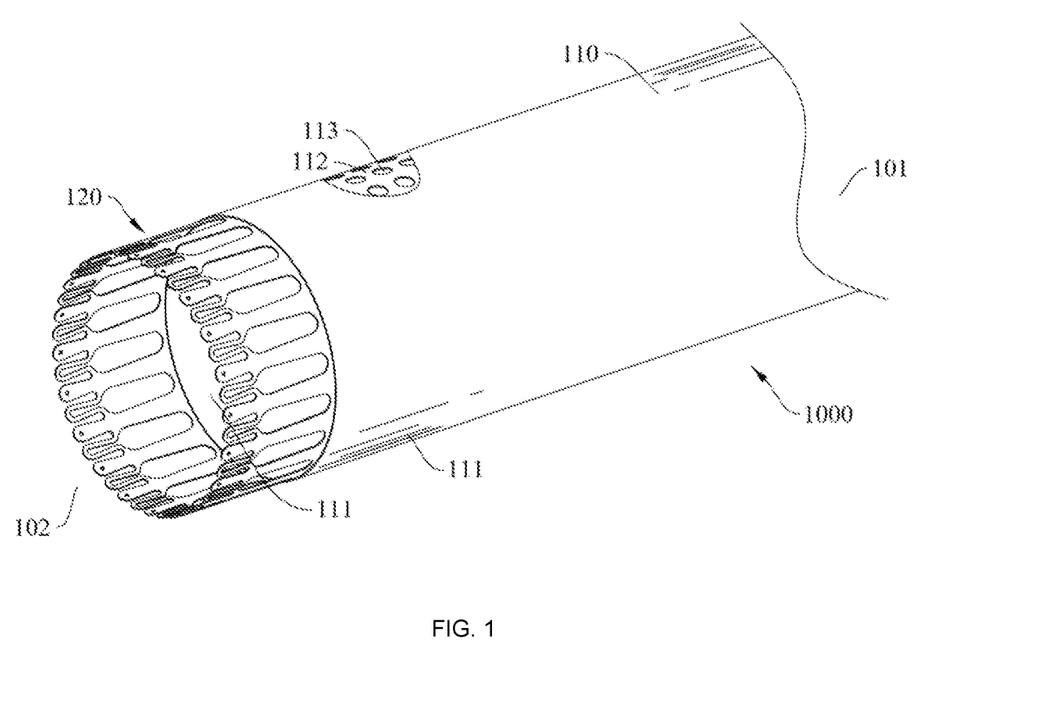
FIG. 1 is a partial schematic view of a sheath (a polymer covering film layer is not shown on an expandable section) in converged configuration according to an embodiment of the present disclosure.
Figure 2:
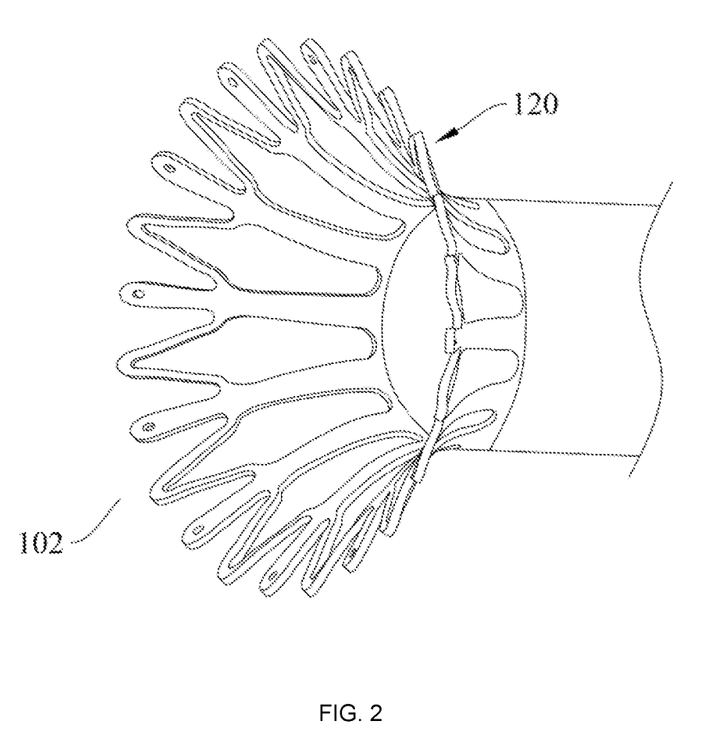
FIG. 2 is a partial schematic view of the expandable section of the sheath in FIG. 1 in flared configuration.

As shown in FIGS. 1 to 6, the present disclosure provides a sheath 1000 for retracting a prosthetic implant, including a tubular body 110. The body 110 has opposing distal end 102 and proximal end 101 in its own axial direction. The distal end of the body 110 is connected with an expandable section 120, and the expandable section 120 has relative converged configuration as shown in FIG. 1 and flared configuration as shown in FIG. 2.

Figure 4:
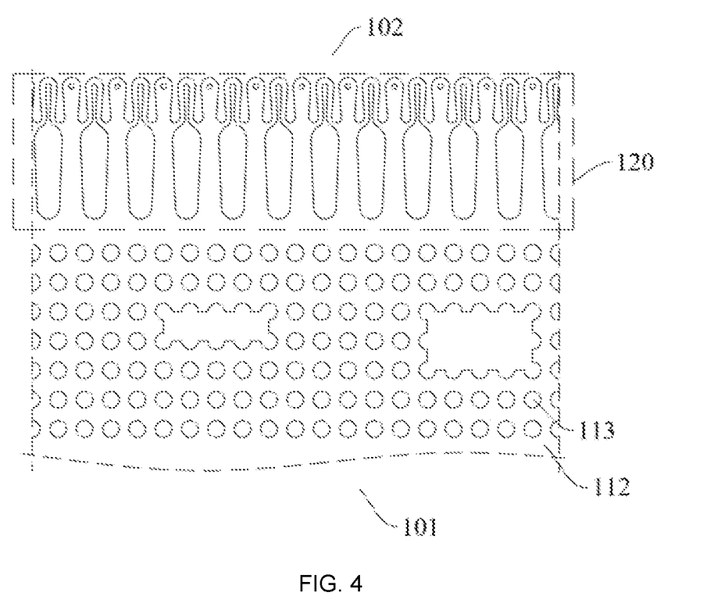
FIG. 4 is a schematic view of the expandable section and the metal reinforcement layer of the sheath in flattened configuration according to an embodiment of the present disclosure.
Figure 5:
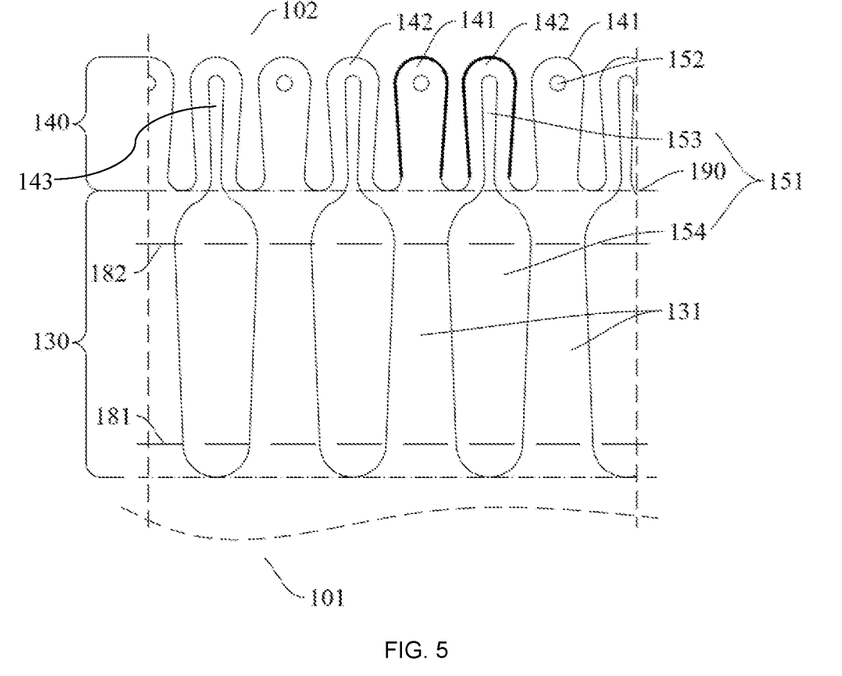
FIG. 5 is a partial schematic view of the expandable section of the sheath shown in FIG. 4.
Figure 6:
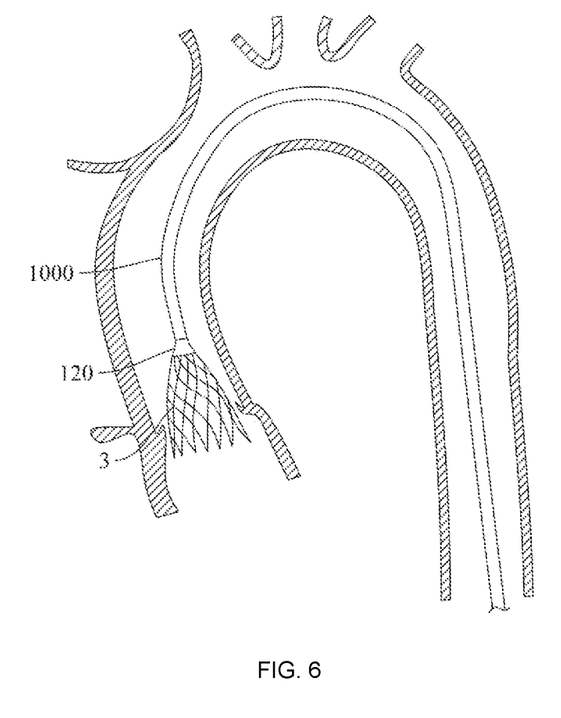
FIG. 6 is a schematic view of a sheath retracting a prosthetic implant in vivo according to an embodiment of the present disclosure.

As shown in FIG. 4 and FIG. 5, the expandable section 120 includes a primary expandable area 130 and a secondary expandable area 140 distributed from the proximal end 101 to the distal end 102 in sequence. The primary expandable area 130 and the secondary expandable area 140 are distinguished by the dash-dotted line 190 as shown in FIG. 5.

The primary expandable area 130 includes a plurality of first expandable pieces 131 arranged at intervals in the circumferential direction of the body 110. The secondary expandable area 140 includes a plurality of second expandable pieces arranged at intervals in the circumferential direction of the body. All the second expandable pieces are divided into two alternating groups, in which the first group is formed by further extending the respective first expandable pieces 131 to the distal end 102, and the second group is formed by connecting strips 142 wound between two adjacent first expandable pieces 131. The first group consists of elastic tabs 141. The proximal end of the elastic tab is connected with the first expandable piece 131.

The distal end of the first expandable piece 131 and the proximal end of the second expandable piece are located on the dash-dotted line 190. When the expandable section 120 is in the flared configuration, each expandable piece has a respective flare angle relative to the axial direction of the body. Similarly, the expandable area where the expandable pieces are located can also be said having a flare angle.

In the converged configuration, the expandable section 120 has an approximately straight cylindrical shape. In the flared configuration, the connecting strip at least pulls the distal ends of the first expandable pieces 131 so as to define the flare angles of the first expandable pieces, while the distal ends of the second expandable pieces are free so that the flare angle of the secondary expandable area is greater than that of the primary expandable area.

Figure 3:
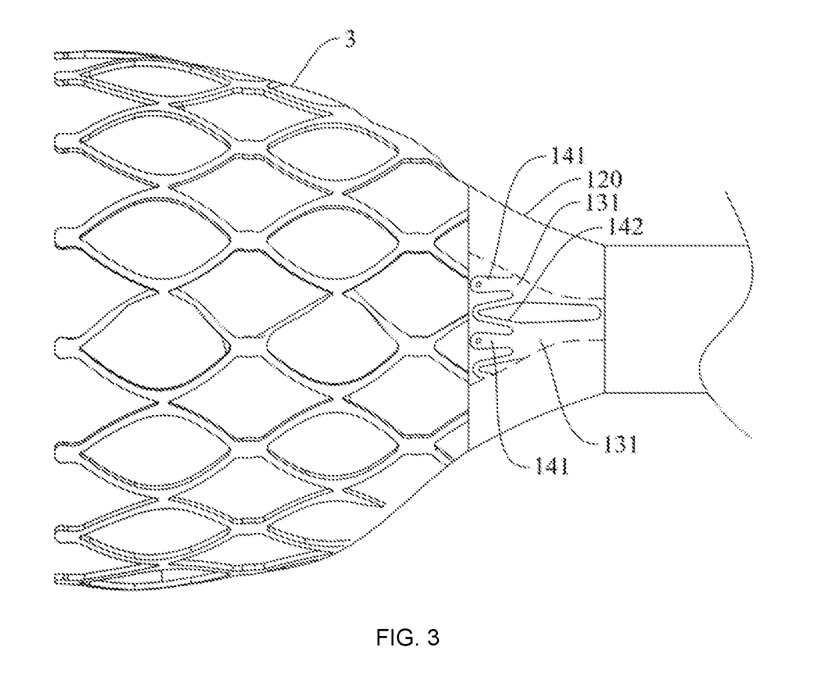
FIG. 3 is a partial schematic view of the sheath retracting a prosthetic implant according to an embodiment of the present disclosure.

During the retraction process, the secondary expandable area 140 conforms to the profile of the prosthetic implant with a larger flare angle, to guide the prosthetic implant rapidly at the initial stage, so that the prosthetic implant can smoothly enter the primary expandable area 130 until being completely received in the sheath, which improves the smoothness of retraction.

The elastic tab 141 is connected with the first expandable piece 131, and under the pulling of the connecting strip 142, a sharp corner would not be formed at the joint of the first expandable piece and the elastic tab, so as to ensure the smoothness of retraction.

In one embodiment, all the second expandable pieces have the same outer contour and are uniformly spaced in the circumferential direction. In other words, the outer contour of the elastic tab 141 is the same as that of the connecting strip 142 (see the thickened lines in FIG. 5). In the axial direction of the body, the distal ends of the elastic tab 141 and the connecting strip 142 are flush with each other. The first group is provided with contrast element(s) adjacent to the distal end thereof.

In one embodiment, the first expandable piece 131 gradually narrows from the proximal end 101 toward the distal end 102 until the respective second expandable piece in the second group, while the outer contour of the second expandable piece gradually widens from the proximal end 101 to the distal end 102, so as to adapt to the deformation and flare of various portions, and also ensure the structural strength.

The distal end of the first expandable piece 131 is the narrowest portion thereof. In one embodiment, the end of the connecting strip 142 is connected to the joint of the first expandable piece 131 and the elastic tab 141 so that the connection of the connecting strip 142 with the joint is chamfered, so as to adapt to the deformation of the connecting strip 142 during flare. Meanwhile, the connecting strip 142 also strengthens the structural strength of the connection, and can restrict the flare of the elastic tab 141, thereby avoiding a sharp corner at the connection.

Both radially inner and outer sides of the expandable section are provided with polymer covering film layers, and the polymer covering film layers on the inner and outer sides are connected at the distal end of the expandable section. The polymer covering film layer has lubricity, facilitating the retraction of prosthetic implant.

In one embodiment, within the secondary expandable area 140, the second expandable piece in the first group (i.e., the elastic tab 141) has a second hollow area 152 adjacent to the distal end thereof, and the second expandable piece in the second group (i.e., the connecting strip 142) has a third hollow area 153. Within the primary expandable area 130, a fourth hollow area 154 is defined between two adjacent first expandable pieces 131.

The hollow areas facilitate the attachment of the inner and outer polymer covering film layers 111. The third hollow area 153 has a larger area than the second hollow area 152, so as to ensure the structural strength of the secondary expandable area 140 and adapt to the deformation and flare of the connecting strip 142.

The fourth hollow area 154 has a larger area than the third hollow area 153. Specifically, the area of the third hollow area 153 is 5-15% of the area of the fourth hollow area 154.

In one embodiment, the third hollow area 153 communicates with the fourth hollow area 154 to form a first hollow area 151. In other words, two adjacent first expandable pieces 131 and the corresponding second expandable pieces (i.e., the connecting strips) enclose the first hollow area 151, so as to adapt to the deformation and flare between adjacent expandable pieces within respective expandable areas. In the axial direction of the body, the length of the first hollow area 151 is greater than 90% of the length of the expandable section.

The above-mentioned comparison between the hollow areas is done in the converged configuration of the expandable section.

In the converged configuration, the expandable section 120 is straight cylindrical and the outer periphery thereof has a circumference, i.e., the total circumference described below.

As shown in FIG. 5, the distal and proximal ends of the first expandable piece 131 are chamfered. The expandable section 120 has a first position 181 and a second position 182 in the axial direction. At the first position 181, the sum of the circumferences of all first expandable pieces 131 accounts for 50%-65% of the total circumference. At the second position 182, the sum of the circumferences of all first expandable pieces 131 accounts for 35%-50% of the total circumference. In the axial direction of the body, the length of the first expandable piece 131 accounts for 60-80% of the length of the expandable section 120.

In one embodiment, the connecting strip 142 is wound in an Ω shape, with the opening 143 of the Ω shape faces towards the proximal side. During retraction, the opening 143 becomes larger, and thus the two ends of the connecting strip 142 move away from each other so that the distal end of the connecting strip 142 moves proximally.

Referring again to FIG. 1, in one embodiment, the body 110 further includes a metal reinforcement layer 112 formed in one piece with the expandable section and connected at the proximal end of the expandable section 120. The expandable section 120 and the metal reinforcement layer 112 can be formed by cutting one piece of tube. The metal reinforcement layer 112 is a non-expandable section, that is, the metal reinforcement layer 112 does not flare when retracting the prosthetic implant.

Both inner and outer sides of the metal reinforcement layer 112 are provided with polymer covering film layers 111. The metal reinforcement layer 112 is provided with fifth hollow areas 113 for the attachment of the inner and outer polymer covering film layers 111. The polymer covering film layer 111 is made of a transparent material. For illustration, the polymer covering film layer in FIG. 1 is shown in an opaque form.

Figure 7:
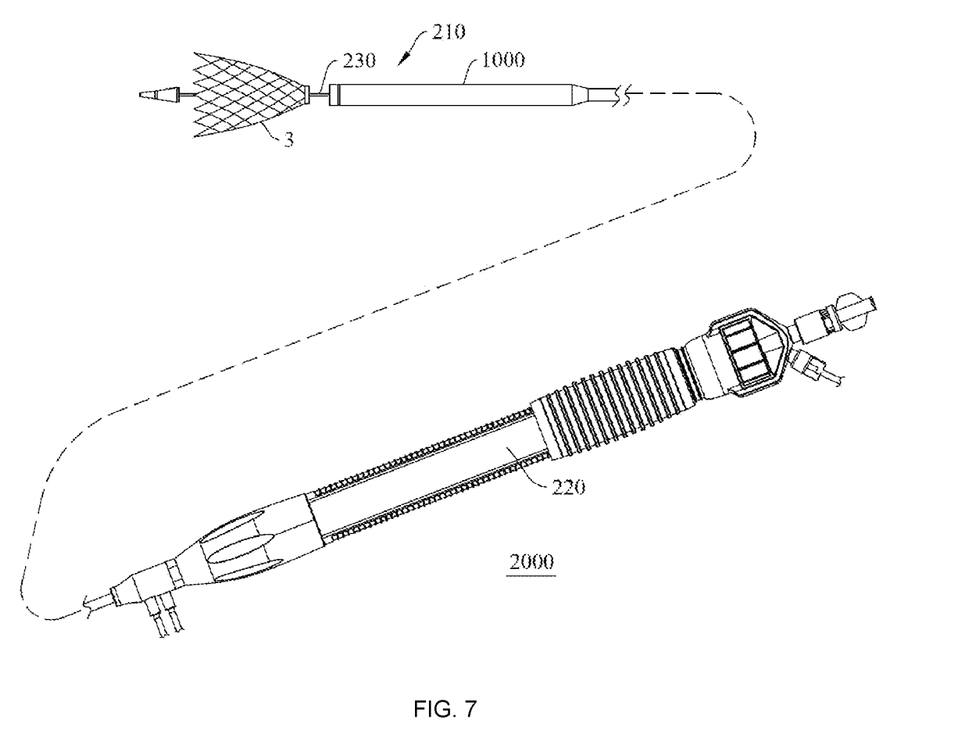
FIG. 7 is a schematic view of a delivery system according to an embodiment of the present disclosure.

As shown in FIG. 7, the present disclosure further provides a delivery system 2000, including a catheter assembly 210 and a control handle 220. The catheter assembly 210 includes the sheath 1000 according to the above-mentioned embodiments and an inner shaft assembly 230. The prosthetic implant is connected to the distal end of the inner shaft assembly 230. The sheath 1000 has an initial state of covering the prosthetic implant, and a release state in which it is moved relative to the inner shaft assembly 230 so as to completely expose the prosthetic implant. The proximal end of the catheter assembly 210 is connected to the control handle 220 in a controllable manner. The specific structure of the catheter assembly and the control handle can use the existing techniques.

The retraction process is described in detail below:

The control handle 220 drives the sheath 1000 to move distally, so that the sheath 1000 moves axially relative to the inner shaft assembly 230, and the expandable section of the sheath acts on the prosthetic implant 3 until the prosthetic implant is completely retracted into the sheath.

By means of the sheath of the present disclosure, during the retraction process, the secondary expandable area conforms to the profile of the prosthetic implant with a larger flare angle, to guide the prosthetic implant rapidly at the initial stage, so that the prosthetic implant can smoothly enter the primary expandable area until being completely received in the sheath, which improves the smoothness of the retraction.

The technical features of the above embodiments can be arbitrarily combined, and not all possible combinations of the technical features of the above embodiments have been described for the sake of brevity of description. However, as long as there is no contradiction in the combination of these technical characteristics, such combination should be regarded as falling into the scope of this specification. When the technical features in different embodiments are shown in the same drawing, it can be considered that the drawing also discloses a combined embodiment of various embodiments involved.

The above-described embodiments only illustrate several embodiments of the present disclosure, and the description thereof is specific and detail, but should not be construed as limiting the scope of the patent disclosure. It should be noted that, for those of ordinary skill in the art, several modifications and improvements can be made without departing from the concept of the present disclosure, all of which fall into the protection scope of the present disclosure.

The invention claimed is:

1. A sheath facilitating retraction of a prosthetic implant, comprising a tubular body which has opposing distal and proximal ends along its own axial direction, wherein the distal end of the body is connected with an expandable section which has a converged configuration and a relative flared configuration and comprises from a proximal end to a distal end of the expandable section in sequence:

a primary expandable area, comprising a plurality of first expandable pieces arranged at intervals in a circumferential direction of the body; and a secondary expandable area, comprising a plurality of second expandable pieces arranged at intervals in the circumferential direction of the body, wherein all the second expandable pieces comprise two alternating groups consisting of a first group and a second group, the second expandable pieces in the first group are formed by further extending the first expandable pieces to the distal end of the expandable section in the axial direction, and each of the second expandable pieces in the second group is wound between and connected to respective junctions at which two adjacent first expandable pieces are connected with respective second expandable pieces in the first group;

wherein in the converged configuration, each of the second expandable pieces in the second group is wound in an Ω shape with an opening, and the opening of the Ω shape faces towards the proximal end of the expandable section; and wherein in the flared configuration, each of the second expandable pieces in the second group has an outer contour that is differently shaped from that of each of the second expandable pieces in the first group.

2. The sheath facilitating retraction of the prosthetic implant of claim 1, wherein in the flared configuration of the expandable section, the primary expandable area and the secondary expandable area have respective flare angles relative to the axial direction of the body, and the flare angle of the secondary expandable area is greater than the flare angle of the primary expandable area.

3. The sheath facilitating retraction of the prosthetic implant of claim 1, wherein in the converged configuration, all the second expandable pieces have the same outer contour and are uniformly spaced in the circumferential direction.

4. The sheath facilitating retraction of the prosthetic implant of claim 3, wherein in the converged configuration, the outer contour of each of the second expandable pieces gradually widens from a proximal end to a distal portion thereof.

5. The sheath facilitating retraction of the prosthetic implant of claim 1, wherein each of the first expandable pieces gradually narrows from a proximal end toward a distal end thereof until being connected with a corresponding second expandable piece in the second group.

6. The sheath facilitating retraction of the prosthetic implant of claim 5, wherein in the axial direction of the body, each of the first expandable pieces has a length being 60-80% of a length of the expandable section.

7. The sheath facilitating retraction of the prosthetic implant of claim 1, wherein two adjacent first expandable pieces and a corresponding second expandable piece in the second group between the two adjacent first expandable pieces enclose a first hollow area, and in the axial direction of the body, the first hollow area has a length being greater than 90% of a length of the expandable section.

8. The sheath facilitating retraction of the prosthetic implant of claim 1, wherein within the secondary expandable area, each of the second expandable pieces in the first group has a second hollow area adjacent to a distal end thereof, and each of the second expandable pieces in the second group has a third hollow area.

9. The sheath facilitating retraction of the prosthetic implant of claim 8, wherein the third hollow area has an area larger than an area of the second hollow area.

10. The sheath facilitating retraction of the prosthetic implant of claim 8, wherein within the primary expandable area, a fourth hollow area is defined between two adjacent first expandable pieces, and the fourth hollow area has an area larger than an area of the third hollow area.

11. The sheath facilitating retraction of the prosthetic implant of claim 1, wherein the body further comprises a metal reinforcement layer formed in one piece with the expandable section, and the metal reinforcement layer is connected with the proximal end of the expandable section.

12. The sheath facilitating retraction of the prosthetic implant of claim 11, wherein the metal reinforcement layer is a non-expandable section.

13. The sheath facilitating retraction of the prosthetic implant of claim 11, wherein inner and outer sides of the metal reinforcement layer are provided with polymer covering film layers, and the polymer covering film layers extend to the distal end of the expandable section to cover inner and outer sides of the expandable section.

14. A delivery system, comprising:
   a catheter assembly, comprising the sheath facilitating retraction of the prosthetic implant of claim 1 and an inner shaft assembly, the prosthetic implant being connected to a distal end of the inner shaft assembly; and
   a control handle, a proximal end of the catheter assembly is connected to and controlled by the control handle.

\* \* \* \* \*